(12) United States Patent
Iaquaniello et al.

(10) Patent No.: US 11,766,637 B2
(45) Date of Patent: Sep. 26, 2023

(54) PROCESS AND RELATING APPARATUS TO MAKE PURE HYDROGEN FROM A SYNGAS ORIGINATED FROM WASTES GASIFICATION

(71) Applicant: NextChem S.p.A., Rome (IT)

(72) Inventors: Gaetano Iaquaniello, Rome (IT); Annarita Salladini, Rome (IT); Elena Antonetti, Rome (IT)

(73) Assignee: NEXTCHEM S.P.A., Rome (IT)

( * ) Notice: Subject to any disclaimer, the term of this patent is extended or adjusted under 35 U.S.C. 154(b) by 783 days.

(21) Appl. No.: 16/344,971

(22) PCT Filed: Oct. 25, 2016

(86) PCT No.: PCT/IT2016/000253
§ 371 (c)(1),
(2) Date: Apr. 25, 2019

(87) PCT Pub. No.: WO2018/078661
PCT Pub. Date: May 3, 2018

(65) Prior Publication Data
US 2020/0078728 A1    Mar. 12, 2020

(51) Int. Cl.
*B01D 53/75* (2006.01)
*B01D 53/047* (2006.01)
(Continued)

(52) U.S. Cl.
CPC .......... *B01D 53/75* (2013.01); *B01D 53/047* (2013.01); *B01D 53/1468* (2013.01);
(Continued)

(58) Field of Classification Search
CPC .. B01D 53/75; B01D 53/047; B01D 53/1468; B01D 2256/16; B01D 2257/304; B01D 2257/504; B01D 53/002; C01B 3/506; C01B 3/52; C01B 3/56; C01B 2203/0475; C01B 2203/0485; C01B 3/50; C10K 1/004; C10K 1/005; C10K 1/003; C10K 1/007; C10K 1/008; C10K 1/028; C10K 1/34;
(Continued)

(56) References Cited

U.S. PATENT DOCUMENTS 5,584,255 A    12/1996    Bishop et al.
6,455,011 B1    9/2002    Fujimura et al.
(Continued)

FOREIGN PATENT DOCUMENTS

CN    103242134    8/2013
WO    WO 2008/068305    6/2008
(Continued)

OTHER PUBLICATIONS

International Search Report, PCT/IT2016/000253, dated Feb. 27, 2017.

*Primary Examiner* — Steven J Bos
(74) *Attorney, Agent, or Firm* — NIXON & VANDERHYE

(57) ABSTRACT

A process and apparatus for producing pure hydrogen from a syngas generated by the high temperature gasification of municipal, agricultural or industrial derived wastes. The process is able to make pure hydrogen to be further reacted with nitrogen to make ammonia and urea.

12 Claims, 4 Drawing Sheets

(51) Int. Cl.
*B01D 53/14* (2006.01)
*C01B 3/50* (2006.01)
*C01B 3/52* (2006.01)
*C01B 3/56* (2006.01)
*C10K 1/00* (2006.01)

(52) U.S. Cl.
CPC ............... *C01B 3/506* (2013.01); *C01B 3/52* (2013.01); *C01B 3/56* (2013.01); *C10K 1/004* (2013.01); *C10K 1/005* (2013.01); *B01D 2256/16* (2013.01); *B01D 2257/304* (2013.01); *B01D 2257/504* (2013.01); *C01B 2203/0475* (2013.01); *C01B 2203/0485* (2013.01)

(58) Field of Classification Search
CPC .......... C10K 3/04; C10K 1/006; Y02C 20/40; Y02P 20/10; Y02P 20/151; C07C 273/04; C10J 3/00
See application file for complete search history.

(56) References Cited

U.S. PATENT DOCUMENTS

| | | |
|---|---|---|
| 6,958,136 B2 | 10/2005 | Chandran et al. |
| 2010/0065782 A1* | 3/2010 | Dierickx ................ C10K 1/165 252/373 |
| 2010/0111783 A1* | 5/2010 | Severinsky ............. C25B 15/08 422/600 |
| 2012/0058921 A1* | 3/2012 | Van Den Berg ....... B01D 53/75 252/373 |
| 2012/0128560 A1* | 5/2012 | Krishnamurthy ...... B01D 53/75 423/220 |
| 2014/0170052 A1* | 6/2014 | Iaquaniello ............... C01C 1/04 423/359 |
| 2014/0364517 A1 | 12/2014 | Selstam et al. |
| 2015/0275112 A1 | 10/2015 | Boissonnet et al. |

FOREIGN PATENT DOCUMENTS

| | | |
|---|---|---|
| WO | WO 2008/130260 | 10/2008 |
| WO | WO 2009/091325 | 7/2009 |
| WO | WO 2009/132449 | 11/2009 |
| WO | WO 2010/112500 | 10/2010 |
| WO | WO2011/008236 | 1/2011 |
| WO | WO 2011/149914 | 12/2011 |

* cited by examiner

PROCESS AND RELATING APPARATUS TO MAKE PURE HYDROGEN FROM A SYNGAS ORIGINATED FROM WASTES GASIFICATION

FIELD OF INVENTION

The present invention relates generally to the conversion of waste materials into chemicals and/or nitrogen based fertilizers. More specifically, the invention provides for methods, systems and apparatus for the purification of a syngas generated by high temperature gasification of waste materials as municipal wastes, refuse derived fuel or industrial wastes to pure Hydrogen.

Such hydrogen could be further reacted with nitrogen to produce ammonia and ammonia in turn could be reacted with CO2 to make urea.

BACKGROUND OF THE INVENTION

Global climate change from one side and growing production of wastes on a worldwide basis from the other, are pushing for questing of new carbon neutral process where wastes can be used as feedstock in alternative to natural gas or other hydrocarbons.

Such processes will have also advantages over bio-diesel and ethanol production because they are not going to compete for farmland that may be needed for food production.

Processes for the production of synthesis gas (syngas) are known in the art. For example, WO2011/008236 A2 discloses the use of plasma gasification or pyrolysis for production of syngas followed by the production of the hydrogen from syngas in a water gas shift (WGS) reactor.

WO 2009/091325 A1 discloses a biomass gasification method and apparatus for production of syngas with rich hydrogen content; and U.S. Pat. No. 5,584,255 discloses a method and apparatus for gasifying organic materials. U.S. Pat. No. 6,958,136 discloses a process for the treatment of nitrogen-containing wastes streams that can generate syngas from carbon sources using alkaline metals and carbon radical formation.

WO 2008130260 A1 discloses a waste to liquid hydrocarbon refinery system designed to convert municipal and industrial wastes, biomass and other carbon-containing feedstock into diesel, gasoline and other products. The system involves a high temperature liquid iron bed that generates row syngas from solid and liquid feedstocks and a very high temperature plasma to convert contaminants in the row syngas into ions.

U.S. Pat. No. 6,455,011 B1 discloses a method and apparatus for treating wastes into two-stage gasification which recovers metals or ash content in the wastes in such a state that they can be recycled and gases containing carbon monoxide (CO) and hydrogen gas ($H_2$) for use as synthesis gas for ammonia ($NH_3$).

CN103242134 discloses an invention related to household garbage treatment method, where the waste is subjected to a thermal cracking to form mixed combustible gases containing CO, $CO_2$, $H_2$, nitrogen ($N_2$) and inert argon (Ar) by a full gasification process. The syngas is purified and separated, and then are used for synthesizing methanol and/or dimethyl eter (DME), generating power and synthesizing urea. The system produces significant amounts of tar which be disposed or used.

US Pat. Number 2014/0364517 A1 discloses a process and system for producing liquid and gas fuels and other useful chemicals from carbon containing source materials comprises cool plasma gasification and/or pyrolysis to produce syngas which in turn could be used for producing hydrocarbon, methanol, ammonia, urea and other products. The system is carbon neutral but is relatively complex and expensive, requires relatively large amount of energy for the plasma gasification and has quite high cost for maintenance.

There remains, therefore, a need for carbon neutral process, apparatus and system for producing hydrogen from carbon containing wastes as municipal, RDF and industrial wastes. Additionally, there remains a need for a process, apparatus and system that has minimal or zero emissions, in particular $CO_2$ emissions.

SUMMARY OF THE INVENTION

According to one aspect of the invention, a process and apparatus for producing pure Hydrogen ($H_2$) is provided in which the process comprises a pre-treatment process to purify the raw syngas and align it to the subsequent conversion/purification steps.

The syngas produced by high temperature gasification of untreated or treated municipal or industrial or agricultural wastes contains few contaminants and components. Although its composition depends on the wastes composition, we could recognize the following family of contaminants/components in the syngas.

Particulates generated from the organic matrix, salts and other metal materials, as lead, chromium, copper and other
a) Chlorine compounds mainly present as HCl
b) Nitrogen compounds present as mainly $N_2$ and traces of HCN and $NH_3$
c) Sulphur compounds present as COS and $H_2S$ with a ratio normally around 1 to 5, lower up to 1 to 10 and low to 1 to 2.
d) Carbon based compounds presents CO and $CO_2$ with a ratio around 3 to 1

Components listed under points a) b) and c) are going to be eliminated from the syngas by a purification process which comprises:
An acidic scrubbing
A basic scrubbing
A treatment with a Wet Electrostatic precipitator (WESP)
A liquid stream is generated throughout such purification step and further treated into a concentration unit where all contaminants are recovered into a solid form.

Such pretreatment will reduce:
Particulate in the range of 1-5 ppm
HCl in the range of 1-5 mg/$Nm^3$
Once preheated the syngas is suitable for the conversion steps where CO is converted into $CO_2$ and $H_2$, in presence of $H_2S$ and COS, and COS is converted into $H_2S$. $H_2S$ is converted into S which leaves the gas into at a liquid and solid state, $CO_2$ is removed via a cryogenic process or amine unit and finally Hydrogen is purified through a Pressure Swing Absorption (PSA) Unit.

An advantage of the present process and apparatus is the ability to purify Hydrogen without any emission of nitrogen and sulphur.

The term "comprises/comprising" when used in this specification is taken to specify the presence or addition of one or more other features, integers, steps, components or groups thereof.

BRIEF DESCRIPTION OF THE DRAWINGS

These and other aspects, features and advantages of which embodiments of the invention are capable of, will be apparent and elucidated from the following description of the embodiments of the present invention, reference being made to the accompanying drawings in which.

DETAILED DESCRIPTION OF THE INVENTION

Specific embodiments of the invention are described with reference to the accompanying drawings. This invention may, however, be embodied in many different forms and should not be constructed as limited to the embodiments set for herein. Rather, these embodiments are provided so that this disclosure will be through and complete, and will fully convey the scope of the invention to those skilled in the art.

Figure 1:
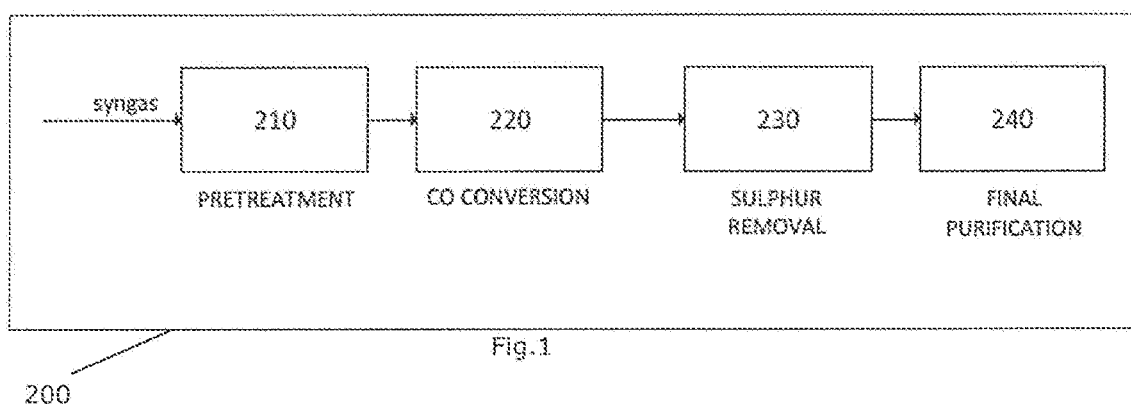
FIG. 1 is a schematic representation of the entire process 200 for making pure $H_2$ from the syngas produced by wastes gasification

An overview of one embodiment according to the invention is shown in FIG. 1.

A raw syngas coming from HT gasification of organic wastes, once cooled in a proper heat recovery boiler or in a quencher is treated in a scrubbing section where, by adding an acidic solution followed by alkaline solution and by a WESP, particulate and chlorine compounds are removed and the syngas is ready for conversion, after its compression. In the conversion step CO is converted into $CO_2$ and $H_2$ by adding steam; $H_2S$ is reduced to sulphur in a solid form, $CO_2$ is removed via cryogenic unit or an amine unit and pure $H_2$ is produced.

Figure 2:
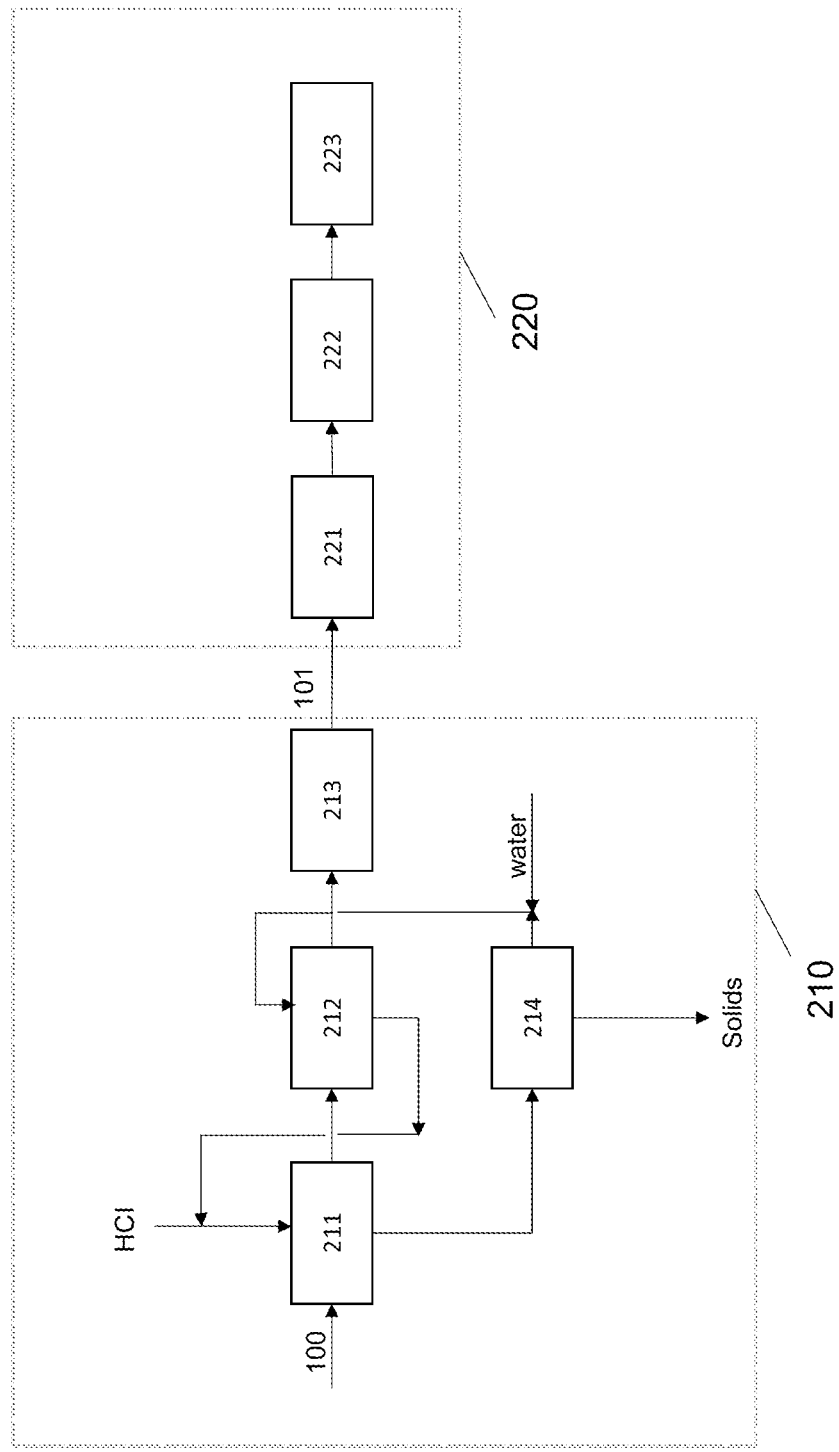
FIGS. 2 and 3 are schematic representations of the syngas treatment, according to FIG. 1, where the unit 200, has been divided into the four main sections 210-220 and 230,240, respectively.
Figure 3:
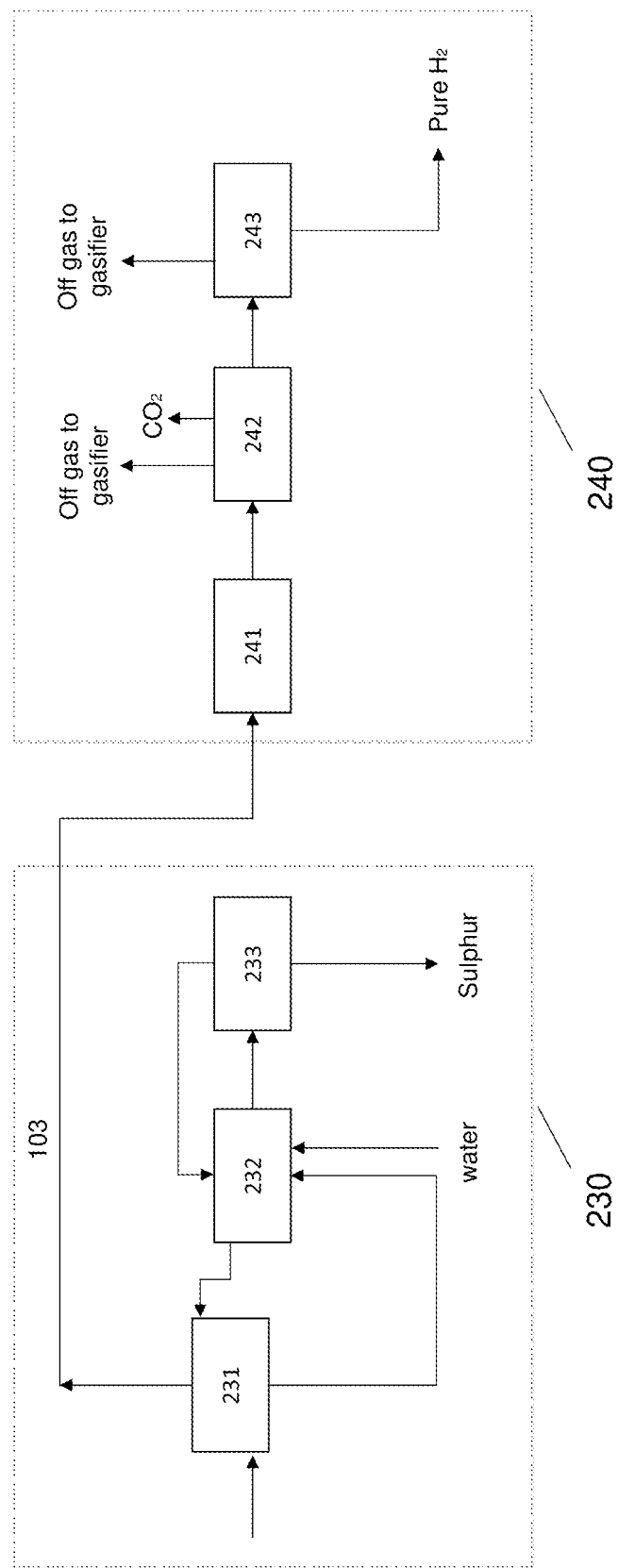
Figure 4:
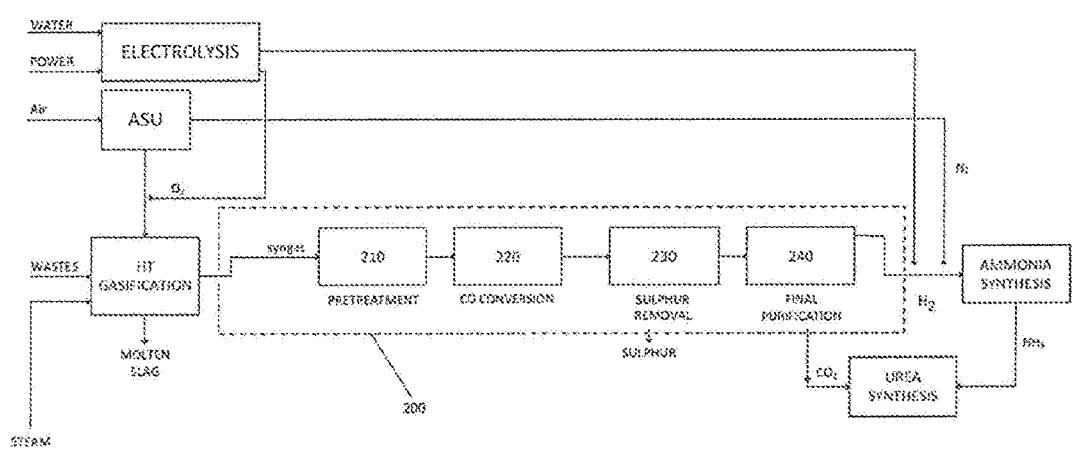
FIG. 4 is an overall block diagram for making urea with H2 obtained by the process of FIG. 1.

A more detailed description of unit 200 is given through FIG. 2. The pretreatment section, 210, the CO conversion section, 220, the $H_2S$ removal section 230 and the $CO_2$ removal and $H_2$ purification section, 240. The subsystem 210 consists of four subunits, the acid scrubbing column, 211, the alcaline scrubbing column, 212, the Wet Electrostatic precipitator (WESP) 213 and liquid stream concentrator, 214. Liquid streams are pumped from one subsection to the another one, and disposed in 214 where contaminants are removed as solid form and water is recycled back.

Section 220 consists of:
Syngas compression, 221
A dechlorination and demetallization section, 222
A high temperature sour shift, section 223, where COS, CO and other components are converted through the following reactions:

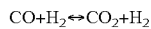

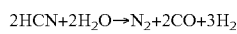

The 230 section may consist of a process or unit, being the content of sulphur in the wastes quite minimal where $H_2S$ is converted into elementary sulphur and separated from the syngas.

Section 230 consists of
An absorbing section, 231 where $H_2S$ is removed from the syngas and transferred into the absorbing liquor
A regeneration section, 232 where absorbing liquor is regenerated and $H_2S$ transformed in S A sulphur recovery section, where S is separated by the liquor and leaves the unit Stream leaving the $H_2S$ removal section, 230, enters the section 240 for the final H2 purification consisting of:
Final sulphur removal, 241 to lower down the sulphur content
Cryogenic unit or amine unit 242, for removing $CO_2$
PSA unit, 243 for making pure $H_2$ In the cryogenic unit, 242 all the $CO_2$ in the syngas is removed and stored in a liquid form. The cryogenic separation of the $CO_2$ is required to purify the $CO_2$ before its use. The off-gas, produced by the unit may be recycled into the gasifier or disposed throughout the combustion chamber of a steam boiler.

Raw hydrogen stream, is further purified by a multi-bed PSA to achieve purity higher than 99.9%. Off-gas, will be recycled to the gasifier or routed to the boiler house.

Pure hydrogen is produced in the range of pressure of 15-30 barg, having compressed the syngas at a pressure of 20-35 barg in section 200.

The invention claimed is:

1. A process for making hydrogen without any emission of nitrogen and sulphur, comprising the following steps:
    gasification in a gasification reactor of a carbon-matrix waste to produce raw syngas, wherein the carbon matrix waste is selected from the group consisting of municipal waste and refuse derived fuel;
    pretreatment (210) of the raw syngas to remove particulates, metals, chlorine, and $NH_3$ compounds, to produce a pretreated syngas;
    conversion (220) where HCN, CO and COS present in the pretreated syngas are converted into $N_2$, $CO_2$ and $H_2S$ in presence of $H_2S$, wherein the conversion comprises a high temperature sour shift reaction (223) where the HCN, COS and CO are converted through the following reactions:

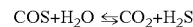

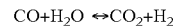

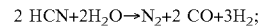

removal (230) where $H_2S$ is removed from the pretreated syngas and then transformed into elementary S; and
    purification (240) where $CO_2$ is removed from the pretreated syngas via a cryogenic unit or an amine unit, and pure hydrogen is produced by a pressure swing absorption unit,
    wherein the method further comprises,
        wherein the $H_2S$ level in the raw syngas by adding waste containing S into the gasification reactor, wherein the increasing is to maintain a concentration high enough to carry out the high temperature sour shift reaction (223).

2. The process according to claim 1 wherein the pretreatment (210) comprises:
    an acid scrubbing (211);
    an alkaline scrubbing of the syngas (212);
    a treatment with a Wet Electrostatic Precipitator (213); and
    a liquid stream concentrator (214)
    wherein the syngas is entering the pretreatment at temperature ranging from 50-200° C. and
    wherein liquid streams are pumped from one subsection to the another one, and disposed in the liquid stream concentrator (214) where contaminants are removed as solid form and water is recycled back.

3. The process according to claim 1 wherein the conversion comprises sequentially, prior to the high temperature sour shift reaction (223):
  syngas compression (221); and
  further dechlorination and demetallization procedure.

4. The process according to claim 1 wherein the removal (230) comprises:
  an absorbing section (231) where $H_2S$ is removed from the syngas and transferred into an absorbing liquor;
  a regeneration section (232) where absorbing liquor is regenerated and $H_2S$ transformed in S; and
  a sulphur recovery section (233) where S is separated by the liquor and leaves the removal step (230).

5. The process according to claim 1 wherein the purification (240) comprises sequentially:
  final further $H_2S$ removal (241) to lower down the sulphur content of a stream leaving the absorbing section (231);
  a cryogenic unit or amine unit (242) for removing $CO_2$; and
  a PSA for final purification of Hydrogen.

6. The process according to claim 5 wherein in the cryogenic unit (242) all the $CO_2$ in the syngas is removed and stored in liquid form.

7. The process according to claim 5 wherein a raw hydrogen stream incoming from the removal step (240) is further purified by a multi-bed PSA to achieve purity higher than 99,9%.

8. The process according to claim 1 wherein the pure hydrogen is produced in the range of pressure of 15-30 barg, having compressed the syngas at a pressure of 20-35 barg in the purification process.

9. The process according to claim 1, wherein Hydrogen is used to make urea throughout the following steps:
  ammonia synthesis where $H_2$, incoming from purification step (240), and $N_2$ are reacted to make ammonia;
  urea synthesis where ammonia and $CO_2$ are reacting to make urea.

10. The process according to claim 1, wherein $CO_2$ in a liquid form leaving the subsection (242) is pumped to an urea synthesis reactor.

11. The process according to claim 3 wherein the pure hydrogen is produced in the range of pressure of 15-30 barg, having compressed the syngas at a pressure of 20-35 barg in the purification process.

12. The process according to claim 4 wherein the pure hydrogen is produced in the range of pressure of 15-30 barg, having compressed the syngas at a pressure of 20-35 barg in the purification process.

* * * * *